US009469879B2

(12) United States Patent
Modiano et al.

(10) Patent No.: US 9,469,879 B2
(45) Date of Patent: Oct. 18, 2016

(54) LYMPHOMA PROGNOSTIC METHODS AND KITS

(71) Applicant: REGENTS OF THE UNIVERSITY OF MINNESOTA, Minneapolis, MN (US)

(72) Inventors: Jaime Freddy Modiano, Roseville, MN (US); Aric Mathew Frantz, Hampton, MN (US); Timothy David O'Brien, Cokato, MN (US); Aaron Lyman Sarver, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 14/410,260

(22) PCT Filed: Mar. 12, 2013

(86) PCT No.: PCT/US2013/030616
§ 371 (c)(1),
(2) Date: Dec. 22, 2014

(87) PCT Pub. No.: WO2013/191756
PCT Pub. Date: Dec. 27, 2013

(65) Prior Publication Data
US 2015/0191790 A1     Jul. 9, 2015

Related U.S. Application Data

(60) Provisional application No. 61/663,156, filed on Jun. 22, 2012.

(51) Int. Cl.
| | | |
|---|---|---|
| *C12Q 1/68* | (2006.01) |
| *A61K 31/196* | (2006.01) |
| *A61K 31/475* | (2006.01) |
| *A61K 31/573* | (2006.01) |
| *A61K 31/655* | (2006.01) |
| *A61K 31/664* | (2006.01) |
| *A61K 31/704* | (2006.01) |
| *A61K 38/50* | (2006.01) |
| *G01N 33/574* | (2006.01) |

(52) U.S. Cl.
CPC ........... *C12Q 1/6886* (2013.01); *A61K 31/196* (2013.01); *A61K 31/475* (2013.01); *A61K 31/573* (2013.01); *A61K 31/655* (2013.01); *A61K 31/664* (2013.01); *A61K 31/704* (2013.01); *A61K 38/50* (2013.01); *G01N 33/57407* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,332,280 B2 | 2/2008 | Levy | |
| 7,622,253 B2 | 11/2009 | Levy | |
| 2011/0152115 A1 | 6/2011 | Staudt et al. | |
| 2014/0302548 A1* | 10/2014 | Sindhi | C12Q 1/6809 435/29 |
| 2015/0225800 A1* | 8/2015 | Lin | C12Q 1/6886 424/649 |

OTHER PUBLICATIONS

Mahadevan D. et al. Transcript Profiling in Peripheral T-Cell Lymphoma, Not Otherwise Specified, and Diffuse Large B-Cell Lymphoma Identifies Distinct Tumor Profile Signatures. Molecular Cancer Therapeutics 4(12)1867-1879, Dec. 2005.*
Jones C. et al. CyclinD1/CyclinD3 Ratio by Real Time PCR Improves Specificity for the Diagnosis of Mantle Cell Lymphoma. J of Molecular Diagnostics 6(2)84-89, May 2004.*
Tamburini B. et al. Gene Expression Profiles of Sporadic Canine Hemangiosarcoma Are Uniquely Associated with Breed. PLoS One 4(5)1-12, May 2009.*
International Search Report and Written Opinion for PCT/US2013/030616, Issued by the European Patent Office on Jul. 29, 2013; 13 pgs.
International Preliminary Report on Patentability for PCT/US2013/030616, issued by the International Bureau of WIPO, on Dec. 31, 2014; 9 pgs.
Alizadeh et al., "Distinct Types of diffuse large B-cell lymphoma identified by gene expression profiling," *Nature*, Feb. 3, 2000;403(6769):503-511.
Breen and Modiano, "Evolutionarily conserved cytogentic changes in hematological malignancies of dogs and humans—man and his best friend share more than companionship," *Chromosome Res.*, 2008;16(1):145-154.
de Hoon et al., "Open Source Clustering Software," *Bioinformatics*, Jun. 12, 2004;20(9):1453-1454.
Flood-Knapik et al., "Clinical, histopathological and immunohistochemical characterization of canine indolent lymphoma," *Vet Compar Oncol*, Dec. 2013;11(4):272-286. First Published Online Feb. 2, 2012.
Fosmire et al., "Inactivation of the p16 Cyclin-Dependent Kinase Inhibitor in High-Grade Canine Non-Hodgkin's T-Cell Lymphoma," *Vet Pathol*, Jul. 2007;44(4):467-478.

(Continued)

*Primary Examiner* — Ralph Gitomer
(74) *Attorney, Agent, or Firm* — Mueting, Raasch & Gebhardt, PA

(57) ABSTRACT

A method for differentiating forms of lymphoma involves analyzing a tumor tissue sample from a subject for expression of CD28, ABCA5, CCDC3, and SMOC2. The CD28:ABCA5 expression ratio differentiates T-cell tumors from B-cell tumors. The CCDC3:SMOC2 expression ratio differentiates different T-cell tumors. The method can further include administering to the subject from whom the sample was obtained an appropriate treatment for the form lymphoma identified by performing the method.

14 Claims, 6 Drawing Sheets

(56) References Cited

OTHER PUBLICATIONS

Frantz et al., "Molecular profiling reveals prognostically significant subtypes of canine lymphoma," *Vet Pathology*, Nov. 2, 2012; 50(4):693-703.
Garrett et al., "Evaluation of a 6-month chemotherapy protocol with no maintenance therapy for dogs with lymphoma," *JVetInternMed*, Nov. 2002;16(6):704-709.
Gomez-Abad et al., "PIM2 imhibition as a rational therapeutic approach in B-cell Lymphoma," *Blood*, Nov. 2011;118(20):5517-5527.
Graves et al., "Antagonistic and Agonistic Anti-canine CD28 Monoclonal Antibodies: Tools for Allogeneic Transplantation," *Transplantation*, Apr. 27, 2011;91(8):833-840.
Gutierrez-Garcia et al., "Gene-expression profiling and not immunophenotypic algorithms predicts prognosis in patients with diffuse large B-cell lymphoma treated with immunochemotherapy," *Blood*, May 2011;117(18):4836-4843.
Iqbal et al., "Molecular signatures to improve diagnosis in peripheral T-cell lymphoma and prognostication in angioimmunoblastic T-cell Lymphoma," *Blood*, Feb. 2010;115(5):1026-1036.
Irizarry et al., "Comparison of Affymetrix GeneChip expression measures" *Bioinformatics*, Apr. 1, 2006;22(7):789-794.
Ito et al., "A tumor-related lymphoid progenitor population supports hierarchial tumor organization in canine B-cell lymphoma," *J Vet Intern Med*, Jul./Aug. 2011;25(4):890-896.
Ito et al., "CD40 ligand is necessary and sufficient to support primary diffuse large B-cell lymphoma cells in culture: a tool for in vitro preclinical studies with primary B-cell malignancies," *Leuk Lymphoma*, 2012;53(7)1390-1398.
Jones et al, "CyclinD1/CyclinD3 Ration by Real-time PCR Improves Specificity for the Diagnosis of Mantle Cell Lymphoma," *JofMolecularDiagnostics*, May 2004;6(2):84-89.
Jubala et al., "CD20 expression in normal canine B cells and in canine non-Hodgkin's Lymphoma," *VetPathol*, Jul. 2005;42(4)468-476.
Lana et al., "Utility of Polymerase Chain Reaction for Analysis of Antigen Receptor Rearrangement in Staging and Predicting Prognosis in Dogs with Lymphoma," *J Vet Intern Med*, Mar.-Apr. 2006;20(2):329-334.
Lenz et al., "Molecular subtypes of diffuse large B-cell lymphoma arise by distinct genetic pathways," *ProcNatlAcadSciUSA*, Sep. 9, 2008;105(36):13520-13525.
Lindblad-Toh et al., "Genome sequence, comparative analysis and haplotype structure of the domestic dog," *Nature*, Dec. 8, 2005;438(7069):803-819.
Loi et al., "Discriminating lymphomas and reactive lymphadenopathy in lymph node biopsies by gene expression profiling," *BMC Medical Genomics, Biomed Central Ltd.*, London UK, Mar. 31, 2011;4(1):27.
Lossos et al., "Prediction of survival in diffuse large-B-cell lymphoma based on the expression of six genes," *NewEnglJMed*, Apr. 29, 2004;350(18):1828-1837.
Mahadevan et al., "Transcript profiling in peripheral T-cell Lymphoma, not otherwise specified, and diffuse large B-cell lymphoma identifies distinct tumor profile signatures," *Molecular cancer Therapeutics*, Dec. 2005; 4(12):1867-1879.
Modiano et al., "Predictive value of p16 or Rb inactivation in a model of naturally occurring canine non-Hodgkin's Lyphoma," *Leukemia*, Jan. 2007;21(1):184-187.
Monti et al., "Molecular profiling of diffuse large B-cell lymphoma identifies robust subtypes including one characterized by host inflammatory response," *Blood*, Mar. 2005;105(5):1851-1861.
Piccaluga et al., "Gene expression analysis uncovers similarity and differences among Burkitt lymphoma subtypes," *Blood*, Mar. 2011;117(13):3596-3608.
Ponce et al., "A morphological study of 608 cases of canine malignant lymphoma in France with a focus on comparative similarities between canine and human lymphoma morphology," *Vet Pathol*, May 2010;47(3):414-433.
Raetz et al., "Gene expression profiling reveals intrinsic differences between T-cell acute lymphoblastic leukemia and T-cell lymphoblastic lymphoma," *PediatrBloodCancer*, Aug. 2006;47(2):130-140.
Rassnick et al., "Comparison of 3 protocols for treatment after induction of remission in dogs with lymphoma," *JVetInternMed*, Nov. 2007;21(6):1364-1373.
Rigacci et al., "Impact of dose-dense immunochemotherapy on prognosis of germinal center and non germinal center origin of diffuse large B cell lymphoma," *JChemother.*, Aug. 2011;23(4):227-231.
Rozen and Skaletsky, "HJ: Primer 3 on the WWW for general users and for biologist programmers," *Bioinformatics Methods and Protocols: Methods in Molecular Biology*, eds. Krawetz S, Misener S. Humana Press; Totowa NJ, 2000: pp. 365-386.
Saldanha, "Java treeview-extensible visualization of microarray data," *Bioinformatics*, Nov. 22, 2004;20(17):3246-3248.
Scott et al., "Molecular subtypes of osteosarcoma identified by reducing tumor heterogeneity through an interspecies comparative approach," *Bone*, 2011;49(3):356-367.
Sorenmo et al. "Outcome and toxicity associated with a dose-intensified, maintenance-free CHOP-based chemotherapy protocol in canine lymphoma: 130 cases," *VetCompOncol.*, Sep. 2010;8(3):196-208.
Staudt and Dave, "The biology of human lymphoid malignancies revealed by gene expression profiling," *AdvImmunol*, 2005;87:163-208.
Tamburini et al., "Gene Expression Profiles of Sporadic Canine Hemangiosarcoma Are Uniquely Associated with Breed," *PLoS One*, 2009;4(5):e5549.
Thomas et al., "Refining tumor-associated aneuploidy through 'genetic recoding' of recurrent DNA copy number aberrations in 150 canine non-Hodgkin lymphomas," *Leuk Lymphoma*, 2011;52(7):1321-1335.
Valli et al., *Classification of hematopoietic Tumors of Domestic Animals*, Second Series ed., AFIP-American Registry of Pathology, Washington D.C., 2002., Cover page, title page and table of contents.
Valli et al., "Veterinary pathologists achieve 80% agreement in application of WHO diagnoses to canine lymphoma," *Cancer Therapy*, Jun. 2008;6:221-226.
Valli et al., "Canine indolent nodular lymphoma," *Vet Pathol.*, May 2006;43(3):241-256.
Valli et al., "Classification of canine malignant lymphomas according to the World Health Organization criteria," *Vet Pathol.*, Jan. 2011;48(1):198-211.
Wright et al., "A gene expression-based method to diagnose clinically distinct subgroups of diffuse large B cell lymphoma," *ProcNatlAcadSciUSA*, Aug. 19, 2003;100(17):9991-9996.
Xia et al., "Analysis of Surviving Expression in the Subtypes of Lymphoma," *The Chinese-German Journal of Clinical Oncology*, Springer, Berlin, Germany, Aug. 2005;4(4):238-243.

\* cited by examiner

A

B

LYMPHOMA PROGNOSTIC METHODS AND KITS

CROSS-REFERENCE TO RELATED APPLICATION

This application is a U.S. National Stage Application of International Application No. PCT/US2013/030616, filed on Mar. 12, 2013, which claims priority to U.S. Provisional Patent Application Ser. No. 61/663,156, filed Jun. 22, 2012, each of which is incorporated herein by reference.

GOVERNMENT FUNDING

This invention was made with government support under P30CA077598, awarded by the National Institutes of Health. The government has certain rights in the invention.

SUMMARY

This disclosure describes, in one aspect, a method that, in general, includes analyzing a tumor tissue sample from a subject for expression of at least two biomarkers, wherein a predetermined ratio of expression of the at least two biomarkers identifies the tumor tissue sample as coming from a subject having a particular subtype of lymphoma.

In some embodiments, the tumor tissue sample analysis can include qRT-PCR.

In some embodiments, the tissue sample can include a fine needle aspirate sample or a biopsy sample.

In some embodiments, the biomarkers being analyzed can include CD28 and ABCA5.

In some embodiments the biomarkers being analyzed can include CCDC3 and SMOC2.

In some embodiments, the biomarkers being analyzed are selected to identify the tumor tissue sample as coming from a subject having a particular subtype of lymphoma with at least 80% accuracy.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

than that of dogs with high-grade B-cell lymphoma. Two dogs classified as 'intermediate' grade were censored from the subgroup analysis in (A) and one dog classified as 'intermediate' grade was censored from the analysis in (B).

Figure 6:
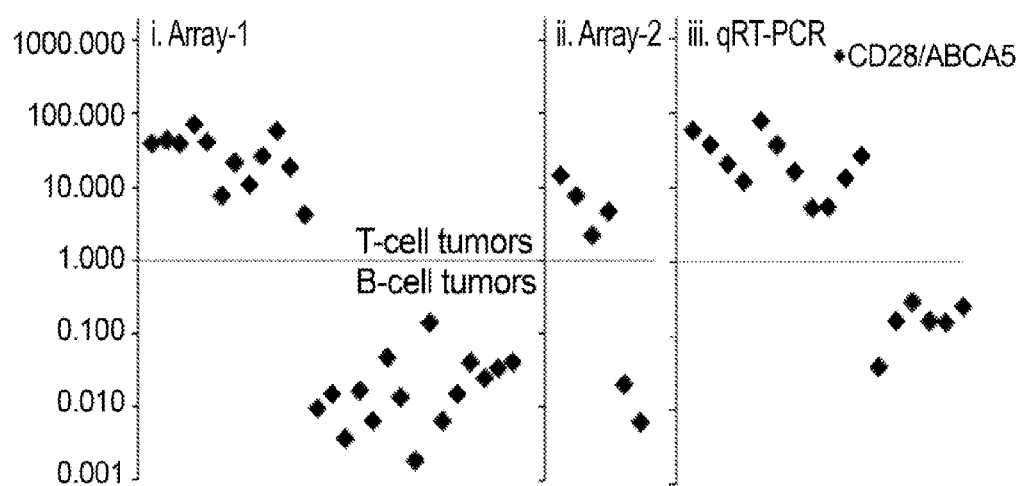
Figure 6:
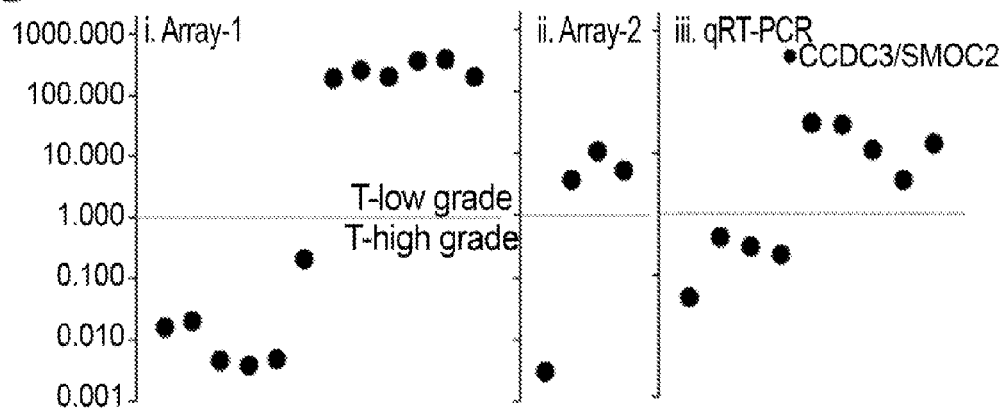

FIG. 6. A four-gene signature accurately classifies canine lymphomas into three molecular subgroups. Array data were surveyed to identify genes that showed robust and significantly different expression between groups and within group variance less than 1.0. For each sample in the array set "i" (N=29) and set "ii" (N=6), the ratio of expression levels for the chosen genes was calculated from normalized array values; an additional validation set "iii" (N=17) included samples that were not part of either gene expression array set, with expression ratios calculated from qRT-PCR values using the formula $\frac{1}{2}^{(Ct[gene-1]-Ct[gene-2])}$. For each sample, qRT-PCR also was done for GAPDH to test confirm RNA integrity. (A) The graph shows the calculated value for the ratio of CD28/ABCA5 in each of the three independent sample sets. This gene expression ratio was greater than 1.0 for T-cell lymphoma samples, whereas it was less than 1.0 for B-cell lymphoma samples in each group. 17/17 samples were correctly identified according to their histologic phenotype (B-cell or T-cell). (B) The graph shows the calculated value for the ratio of CCDC3/SMOC2 for T-cell lymphomas in each the three independent sample sets. This gene expression ratio was greater than 1.0 for low-grade T-cell lymphomas, whereas it was less than 1.0 for high-grade T-cell lymphomas. 9/9 samples are correctly identified according to their histologic classification as low- or high-grade T-cell lymphoma.

DETAILED DESCRIPTION OF ILLUSTRATIVE EMBODIMENTS

This disclosure describes a method to identify and classify subtypes of canine lymphoma using cytology and or histopathology from fine needle aspirates or other tissue biopsies in combination with quantitative reverse transcriptase-polymerase chain reaction (qRT-PCR) technology. We have identified variation in the molecular properties of lymphoma subtypes that allow this stratification of disease into clinically relevant groups. As these groups can have significantly different outcomes and may respond differently to various treatment modalities, there is utility in identifying the specific type of disease for each patient. The process adds information that cannot be obtained from cytological examination alone and is considerably simpler and more efficient e.g., less sample tissue required and/or more cost efficient—than conventional biopsies coupled with immunohistochemistry.

In some embodiments, the method may be performed by analyzing the relative expression of as few as two biomarkers. For example, analyzing the relative expression of the biomarkers CD28 and ABCA5 (ATP-binding cassette subfamily A, member 5) can distinguish whether a lymphoma is a B-cell lymphoma or a T-cell lymphoma. As another example, analyzing the relative expression of the biomarkers CCDC3 (Coiled-coil domain-containing protein 3) and SMOC2 can identify whether a T-cell lymphoma is an aggressive high grade T-cell lymphoma or an indolent low grade T-cell lymphoma. Moreover, these analyses may be combined. That is, analyzing the relative expression of the four biomarkers—e.g., CD28 expression compared to ABCA5 expression, and CCDC3 expression compared to SMOC2 expression—can distinguish B-cell lymphomas, high grade T-cell lymphomas, and low grade T-cell lymphomas. Significantly, the methods described herein can be expanded to other lymphomas and other species. Lymphoma is a commonly diagnosed tumor in dogs. Lymphoma, however, encompasses at least four, and perhaps more than 25 different disease subtypes with different etiologies and different biological behaviors. We show that canine lymphomas can be grouped broadly into four pathological categories, including separation based on immunophenotype (i.e., B-cell or T-cell) and histological grade (i.e., high-grade or low-grade). Generally, high-grade T-cell lymphomas such as, for example, lymphoblastic T-cell lymphoma (LBT) or peripheral T-cell lymphoma, not otherwise specified (PTCL) can show aggressive biological behavior and poor response to therapy. In contrast, low-grade T-cell lymphomas can show indolent behavior and often require no therapy or only low intensity therapy. Dogs with low-grade T-cell lymphomas may not benefit from aggressive multiagent chemotherapy.

Existing diagnostic methods include, for example, the PCR for Antigen Receptor Rearrangement (PARR) test, which can determine lymphoma phenotype, i.e., whether the lymphoma involves a tumor of B-cells or T-cells. The PARR test is performed using a peripheral blood sample or a fine needle aspirate from a lymph node. The PARR test, however, cannot distinguish between lymphoma subtypes, even when combined with cytology, beyond simple T-cell versus B-cell phenotyping.

Our method uses a validated a set of rules that allow one to subdivide lymphomas into phenotypically distinct categories—i.e., B-cell versus T-cell—and prognostically significant categories—e.g., aggressive T-cell lymphoma versus indolent T-cell lymphoma versus B-cell lymphoma. Our method can therefore provide additional and complementary diagnostic information to veterinary caregivers that can include prognostic information and guide therapy decisions. Thus, we have developed a method that involves qRT-PCR that have broad application in the diagnostic laboratory industry, can be performed rapidly, and, when combined with cytological diagnoses, can expand prognostic information for dogs at an acceptable cost.

In some cases, the method can include measuring expression of an internal reference. Typically, the internal reference expression can serve as a control—e.g., a verified/validated control prepared under GMP or GMP-like conditions by the performing lab or by a contractor. Such a control may be obtained from a tissue biopsy that is known to show histological changes characteristic of a condition and/or retain the appropriate signature. An exemplary negative control could include, for example, normal peripheral blood lymphocytes.

Significantly, our method may be extended to human non-Hodgkin lymphomas (NHL). We have previously utilized canine microarray datasets to uncover patterns of gene expression in human disease where they were otherwise undetectable (Scott et al. Bone. 2011; 49(3):356-367). Here, our canine datasets can isolate changes in gene expression between disease subtypes that will have prognostic utility in human disease. Our method provides proof of concept for developing similar tests that can distinguish between different subtypes of, for example, NHL disease. For example, one could use the method described herein to distinguish between B-cell NHL (the most common type) and T-cell NHL (an infrequent type that currently can only be distinguished using immunological approaches). As another example, the method described herein may distinguish pathologically high-grade subtypes of T-cell NHL such as peripheral T-cell lymphoma—not otherwise specified (PTCL-NOS) from pathologically low grade subtypes of T-cell NHL such as angioimmunoblastic T-cell lymphoma (AITL). In this example, the progression and management of these two diseases is significantly different: PTCL-NOS shows rapid tumor progression, whereas morbidity and mortality in patients with AITL is due to immune dysfunction.

Gene Expression Profiling Stratifies Canine Lymphoma into Three Major Subgroups

Canine lymphomas can be classified into multiple subtypes according to modified WHO criteria (Valli et al. Vet Pathol. 2011; 48(1):198-211). We sought to determine if these subtypes also could be distinguished at the molecular level. Initially, we profiled gene expression in samples from cohort-1, which included four samples of lymphoblastic T-cell lymphoma (LBT), three samples of peripheral T-cell lymphoma, not otherwise specified (PTCL), six samples of T-zone lymphoma (TZL), two samples of Burkitt's lymphoma (BL), eight samples of diffuse large B-cell lymphoma (DLBCL), five samples of marginal B-cell lymphoma (MZL), and one non-T-cell, non-B-cell lymphoma (NT-NBL). Thus, in all, we examined 13 T-cell lymphoma samples, 15 B-cell lymphoma samples, and one non-T-cell, non-B-cell lymphoma sample.

Figure 1:
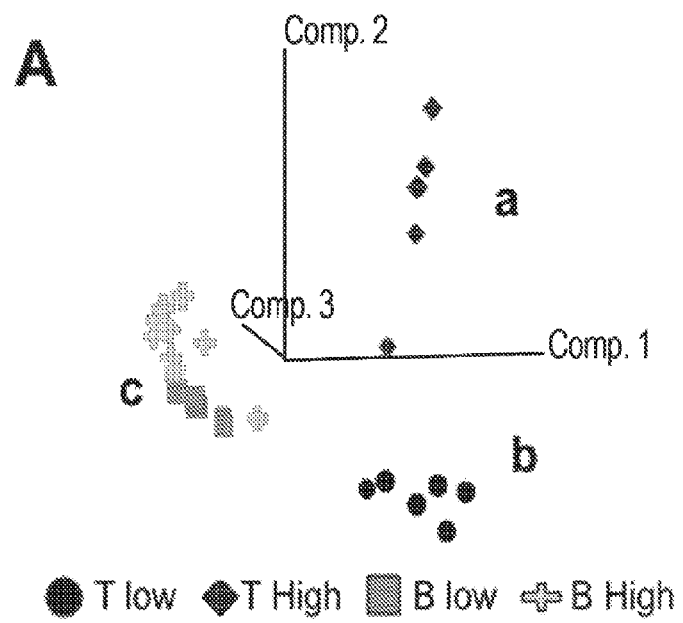
FIG. 1. Three molecular groups are identifiable in canine lymphoma samples using gene expression profiling. (A) Principal component analysis of normalized gene expression profiles of canine high-grade T-cell lymphoma, low-grade T-cell lymphoma, and B-cell lymphoma. Symbols for each group are as shown in the legend. (B) Heat map showing expression data for genes (N=859) with variance greater than 1.0 and greater than eight-fold change in at least three profiles. Colors represent median-centered fold change expression following $\log_2$ transformation (a quantitative representation of the colors is provided in the scale at the bottom). Upregulated genes are assigned values greater than 0.0; down regulated genes are assigned values less than 0.0.
Figure 1:
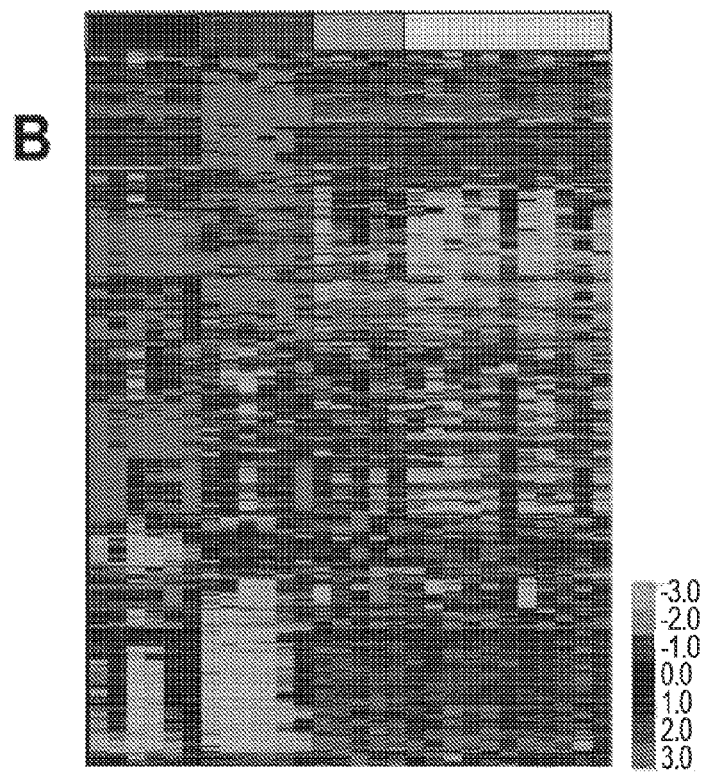

FIG. 1A shows unsupervised principal component analysis (PCA) of expression data from these samples. Three groups (a, b, c) are discernible, separated along the three principal components. Group (a) represents dogs with LBT and PTCL (N=7). Group (b) represents dogs with TZL (N=6). Group (c) represents dogs with B-cell malignancies (N=15). The NTNBL sample appears to be most closely related to T-cell lymphomas, but does not segregate into any of the three groups (data not shown). Differences in gene expression underlying this stratification are observable using unsupervised hierarchical clustering with a heat map showing 859 genes with variance greater than 1 and with greater than 8-fold difference in expression across three or more samples (FIG. 1B).

Thus, LBT and PTCL form a single molecular group (referred to hereinafter as "high-grade T-cell lymphoma" or "T-high"). TZL forms a distinct molecular group (referred to herein as "low-grade T cell lymphoma" or "T-low"). Segregation among B-cell tumors was more subtle. It was challenging to separate out BL and DLBCL samples (referred to herein as "high-grade B-cell lymphoma" or "B-high") from MZL samples (referred to herein as "low-grade B-cell lymphoma" or "B-low"), although MZLs formed a subcluster in the PCA.

Figure 2:
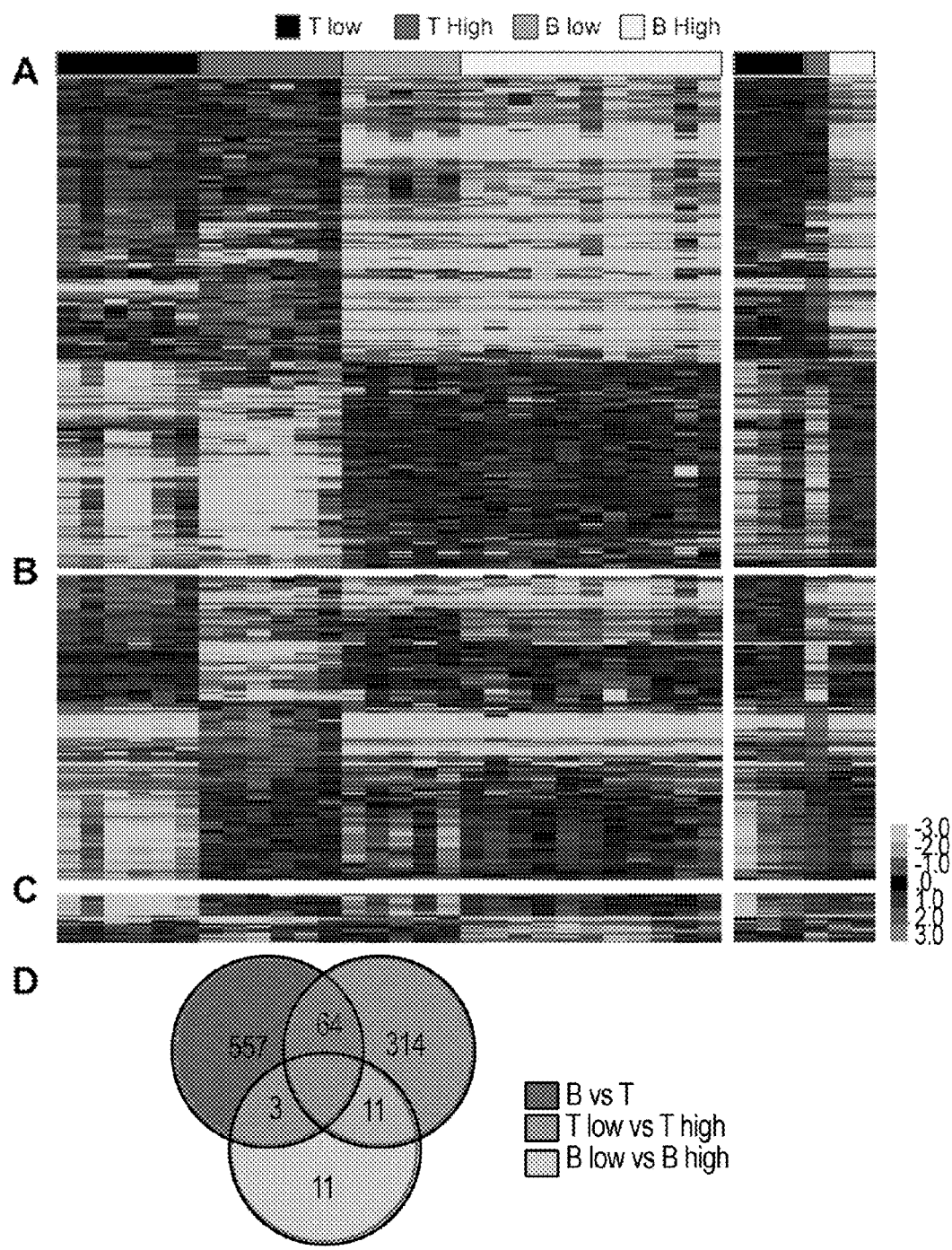
FIG. 2. Statistically significant genes define molecular subtypes of canine lymphoma. Genes differentially expressed with greater than three-fold average change and p-values<0.001 were identified for the comparison of groups composed of (A) B-cell and T cell lymphomas (N=624), (B) high-grade and low-grade T-cell lymphomas (N=389), and (C) high-grade and low-grade B-cell lymphomas (n=25) using T-test statistics. The second panel of (A-C) is an independent "validation" set (6 samples, right inset) of the results obtained in the initial set (29 samples, left panel). (D) Venn diagram showing the number of unique and overlapping genes for each 2-group test.

FIG. 2A recapitulates the heat map shown in FIG. 1B, except that using a 2-group t-test (BH q≤0.001) identifies 624 differentially expressed genes distinguishing T-cell lymphomas from B-cell lymphomas. FIG. 2B shows 389 differentially expressed genes that distinguish the T-high group from the T-low group; this gene cluster also stratifies samples of high-grade T cell lymphoma from all other lymphomas tested. FIG. 2C shows 25 differentially expressed genes that could help to distinguish between the B-high and the B-low groups. These genes also can distinguish the T-high from the T-low group, and include a subset of the gene cluster in FIG. 2B, as illustrated by the Venn diagram in FIG. 2D, which shows shared genes identified in each two-group analysis.

We next looked at the statistically significant genes identified in cohort-1 in a second independent cohort-2. This cohort consisted of six samples including three samples of TZL, one sample of PTCL, and two samples of DLBCL. The analysis for these samples is shown on the right inset for FIGS. 2A-C. The molecular signatures statistically characterized in the first cohort-1 are observable in cohort-2.

Figure 3:
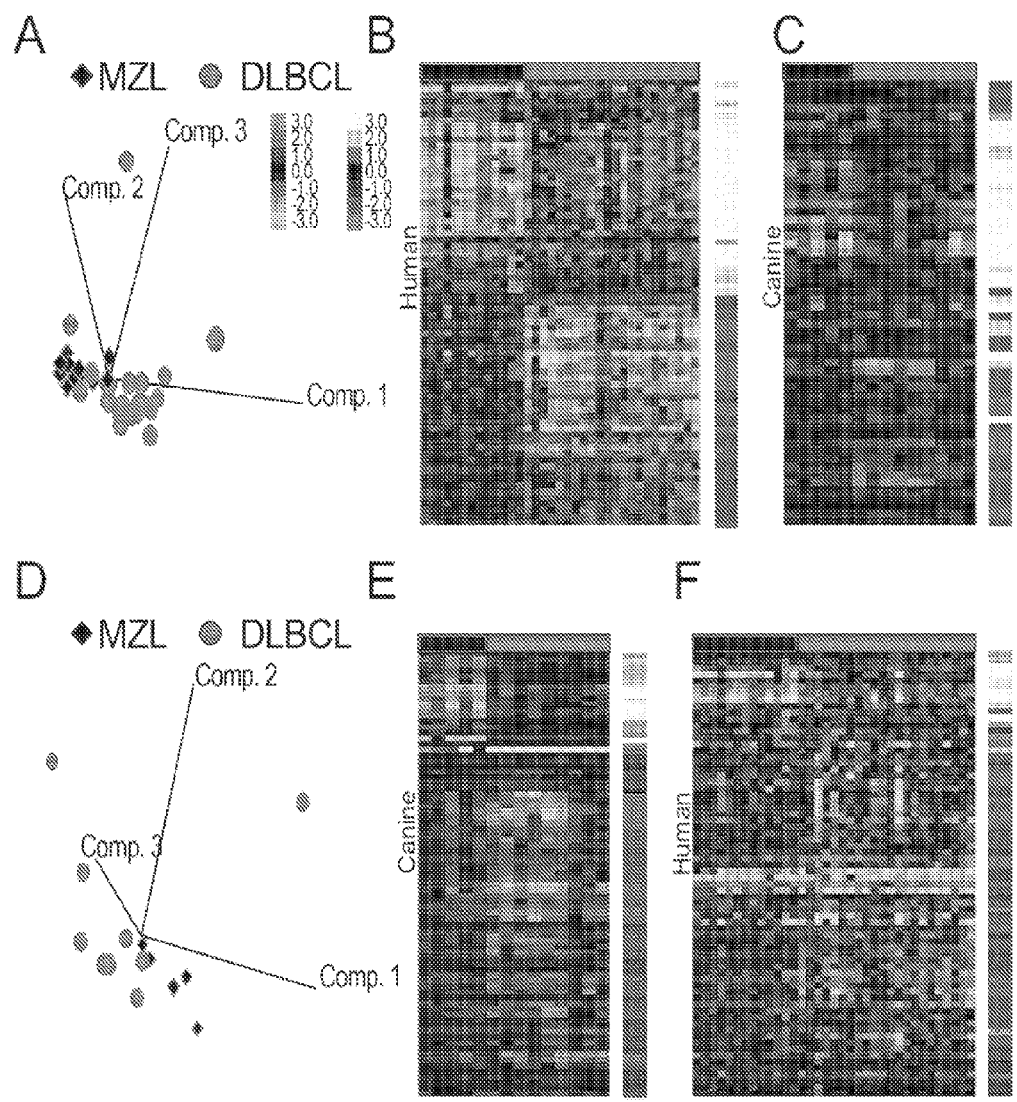
FIG. 3. Orthologous gene expression signatures indicate canine and human B-cell lymphomas are molecularly homologous diseases. (A) Principal components analysis of human MZL and DLBCL cases. (B) Heat map showing differentially expression data for 71 genes in human nodal MZL and DLBCL. (C) 71 human gene vectors from panel B mapped to 56 canine genes and applied to canine MZL and DLBCL samples. (D) Principal components analysis of canine MZL and DLBCL cases. (E) Heat map showing differentially expression data for 79 genes in canine MZL and DLBCL. (F) 79 Canine gene vectors from panel E mapped to 70 human genes and applied to human MZL and DLBCL samples. To track the patterns of expression, we used a "gene vector-based" strategy. Each gene vector is assigned a yellow or blue tag within a toe-bar, where the color denoted its cluster assignment and the intensity reflected the relative variance in expression. The composite gene vectors (toe-bars) thus illustrate the relative conservation of the gene clusters between datasets. The corollary to the hypothesis that the molecular characteristics of DLBCL and MZL in humans and dogs are conserved is that a comparable arrangement of gene vectors that is apparent in datasets from both species.

To more carefully assess the potential for heterogeneity of canine B-cell malignancies, we compared the molecular properties of DLBCLs and MZLs in our sample set, and we extended this comparison to a sample set that included human DLBCLs and MZLs[5] using an approach that we previously applied successfully to define gene expression signatures across different platforms and species (Scott et al. Bone. 2011; 49(3):356-367). There is significant overlap in the morphological features of canine MZL and DLBCL (Valli. Cancer Therapy. 2008; 6:221-226), and these two tumor types also were challenging to stratify according to their molecular signatures (FIG. 2C). We saw comparable results in the human tumors: FIG. 3A shows PCA for human DLBCLs (N=22) and nodal MZLs (N=13). As was true for the canine sample set, MZLs formed an identifiable, relatively homogeneous subgroup. FIG. 3B shows hierarchical clustering of the human samples using the 71 genes with highly statistically significant ($p \leq 10^{-6}$) differential expression between human MZL and DLBCL subtypes. To determine if this signature was retained in the canine samples, we name mapped 37 genes overexpressed in human MZL and 34 genes overexpressed in human DLBCL to their canine homologues, identifying 27 and 29 orthologous genes, respectively. Unsupervised hierarchical clustering of the dog cohort with these human vectors was consistent with the prediction of molecular homology, resulting in similar clustering patterns for MZL and DLBCL to that observed in the human cohort with approximately 90% of the genes remaining in their respective clusters (FIG. 3C). The same analysis was used to examine stratification between canine MZL and DLBCL. FIG. 3D shows PCA for canine DLBCL (N=9) and nodal MZL (N=5) samples, where the latter formed a subgroup that resembled the one seen in the human samples (compare with FIG. 3A). FIG. 3E shows hierarchical clustering of the canine samples using 79 genes with statistically significant ($p \leq 10^{-3}$) differential expression between the canine MZL and DLBCL subtypes (as shown in FIG. 2C). To determine if this signature was retained in the human dataset, we name mapped 62 genes overexpressed in canine MZL and 17 genes overexpressed in canine DLBCL to their human homologues, confidently identifying 55 and 15 orthologous genes in the human dataset, respectively. Unsupervised hierarchical clustering of the human cohort using these canine vectors also was consistent with the prediction of molecular homology, resulting in similar clustering patterns for MZL and DLBCL to that observed in the canine cohort with greater than 80% of the genes remaining in their respective clusters (FIG. 3F).

The sample size used was insufficient to establish segregation of canine DLBCL into the activated B-cell (ABC) and germinal center B-cell (GCB) subtypes defined by Staudt et al. (US Patent Application Publication No. 2011/0152115 A1). The methods described here would be distinct from, and complementary to those described by Staudt et al. in U.S. Patent Application Publication No. 2011/0152115.

Molecular Drivers for Stratification of Canine Lymphomas

Assessment of gene expression differences using ingenuity pathway analysis (IPA) and the 624 genes shown in FIG. 2A revealed segregation of T-cell lymphoma and B-cell lymphoma according to predictable functions including, for example, activation, proliferation, and development of T cells and B cells, respectively (Table 1 and Table 2). Similarly, segregation of high-grade T-cell from low-grade T-cell tumors was based on enrichment of cell cycle related genes (principally chromosomal segregation and mitosis, Table 3). The low-grade T-cell tumors, in contrast, showed enrichment for functions associated with T-cell activation and survival (Table 4). As noted above, the molecular signatures separating B-cell tumors were less robust. A subset of genes that was enriched in the high-grade T-cell tumors—associated with cell division and chromosome segregation—also was enriched in high-grade B-cell tumors. Intriguingly, IPA also showed enrichment of functions associated with T-cell signaling in the low-grade B-cell tumors.

TABLE 1

Functional pathways enriched in T-cell lymphoma (vs. B-cell lymphoma)

| Functions | p-Value |
| --- | --- |
| Proliferation of lymphocytes | $8.95 \times 10^{-25}$ |
| Proliferation of immune cells | $4.21 \times 10^{-24}$ |
| Proliferation of T lymphocytes | $3.41 \times 10^{-23}$ |
| Immune response | $1.79 \times 10^{-22}$ |
| Cell death of immune cells | $2.99 \times 10^{-22}$ |

TABLE 2

Functional pathways enriched in B-cell lymphoma (vs. T-cell lymphoma)

| Functions | P-Value |
| --- | --- |
| Proliferation of B lymphocytes | $7.84 \times 10^{-17}$ |
| Developmental process of B lymphocytes | $1.06 \times 10^{-15}$ |
| Quantity of B lymphocytes | $1.51 \times 10^{-15}$ |
| Proliferation of B lymphocytes | $2.06 \times 10^{-15}$ |
| Antibody response | $5.35 \times 10^{-12}$ |

TABLE 3

Functional pathways enriched in high-grade T-cell lymphoma (vs. low-grade T-cell lymphoma)

| Functions | p-Value |
| --- | --- |
| Cell division process of chromosomes | $1.58 \times 10^{-23}$ |
| Segregation of chromosomes | $2.29 \times 10^{-18}$ |
| Mitosis | $1.11 \times 10^{-13}$ |
| Ploidy | $3.02 \times 10^{-11}$ |
| Cell cycle progression | $5.18 \times 10^{-11}$ |

TABLE 4

Functional pathways enriched in low-grade T-cell lymphoma (vs. high-grade T-cell lymphoma)

| Functions | p-Value |
| --- | --- |
| Survival of T lymphocytes | $3.19 \times 10^{-8}$ |
| Activation of cells | $8.58 \times 10^{-8}$ |
| Survival of lymphocytes | $2.52 \times 10^{-7}$ |
| Survival of blood cells | $2.54 \times 10^{-7}$ |
| Cell death of immune cells | $2.60 \times 10^{-7}$ |

We confirmed the IPA results using gene set enrichment analysis (GSEA). We first examined genes that were differentially expressed between B-cell and T-cell lymphoma subtypes and obtained results similar to the results obtained using IPA. The same was true when we analyzed differences between T-high tumors and T-low tumors. Assessment of the B-high group versus the B-low group provided further evidence of gene enrichment in T-cell signaling pathways.

Figure 4:
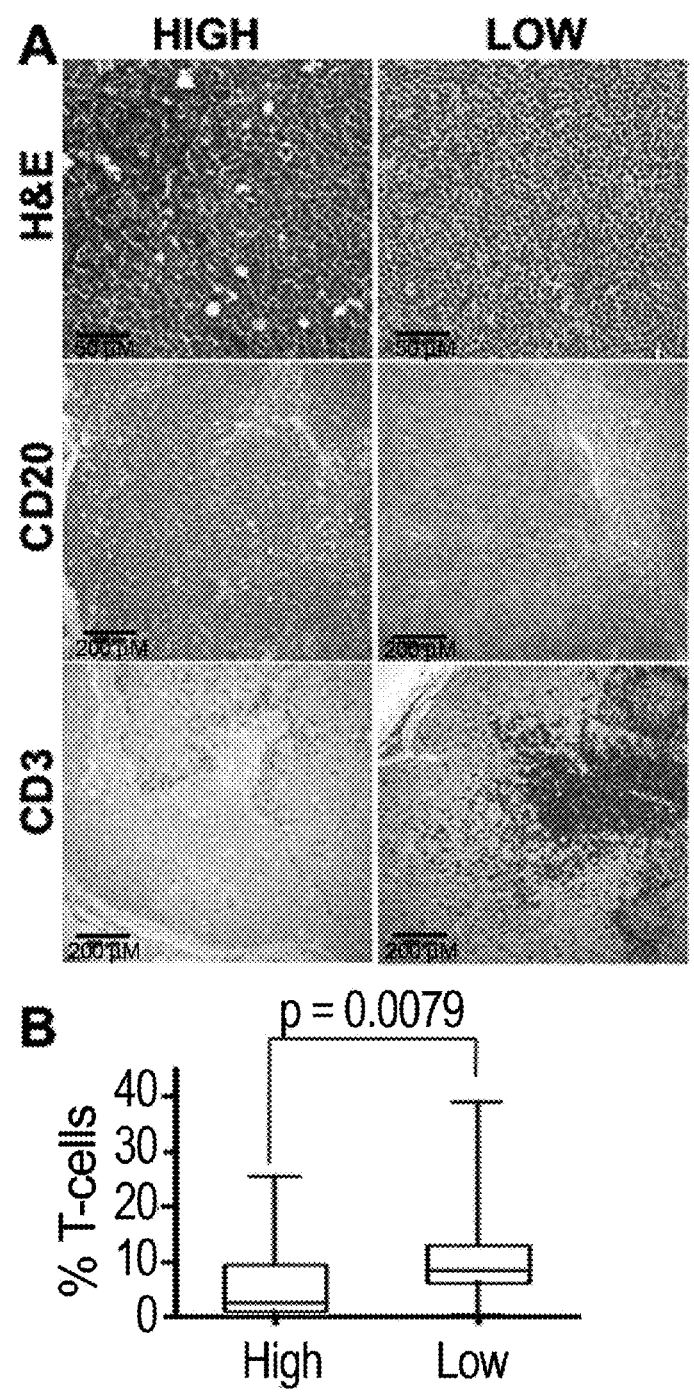
FIG. 4. Residual or infiltrating T cells are enriched in canine MZL. (A) Photomicrographs from a DLBCL sample ("High," left) and an MZL sample ("Low, right") stained with HE (top), anti-CD20 (middle), or anti-CD3 (bottom) to assess the immunophenotype of cells within the tumor. HE magnification=400× (size bar=50 μm); IHC magnification=100× (Size bar=200 μm). (B) Forty-eight independent samples of canine B-cell lymphoma (28 high-grade tumors and 20 low-grade tumors) were immunophenotyped by flow cytometry using antibodies against CD3, CD5, CD21, and CD22. The frequency of T cells and B cells was enumerated from analysis of more than 10,000 cells per sample. The box-plot provides a visual summary of the data. The bottom and top edges of the boxes correspond to the sample $25^{th}$ and $75^{th}$ percentiles, and the box lengths represent one interquartile range. The centerlines correspond to the sample medians, and the "whiskers" projecting from the boxes extend to the farthest outliers. The two groups were statistically significantly different (p=0.0079).

Similar enrichment of T cell signatures in B cell disease has been reported for subsets of human DLBCL (Alizadeh et al. Nature. 2000; 403(6769):503-511; Monti et al. Blood. 2005; 105(5):1851-1861). Thus, we investigated the possibility that the IPA and GSEA data highlighted signatures of residual or infiltrating T cells associated with our low-grade B-cell lymphomas. We performed immunohistochemistry on the tumors from this cohort, as well as immunohistochemistry and flow cytometry on an independent series of B-high tumors and B-low tumors to quantify T cells in B-cell lymphomas. FIG. 4A shows examples of DLBCL and MZL samples stained for CD3 and CD20 that illustrate the relative T-cell enrichment that was seen recurrently in MZLs. FIG. 4B shows the data quantitatively: the box and whisker plot describes the relative abundance of T cells in high-grade B-cell lymphomas (N=28) versus low-grade B-cell lymphomas (N=20). There was a significant difference (p=0.0079) between these two lymphoma subgroups with regard to the abundance of T cells present in the tumors.

Figure 5:
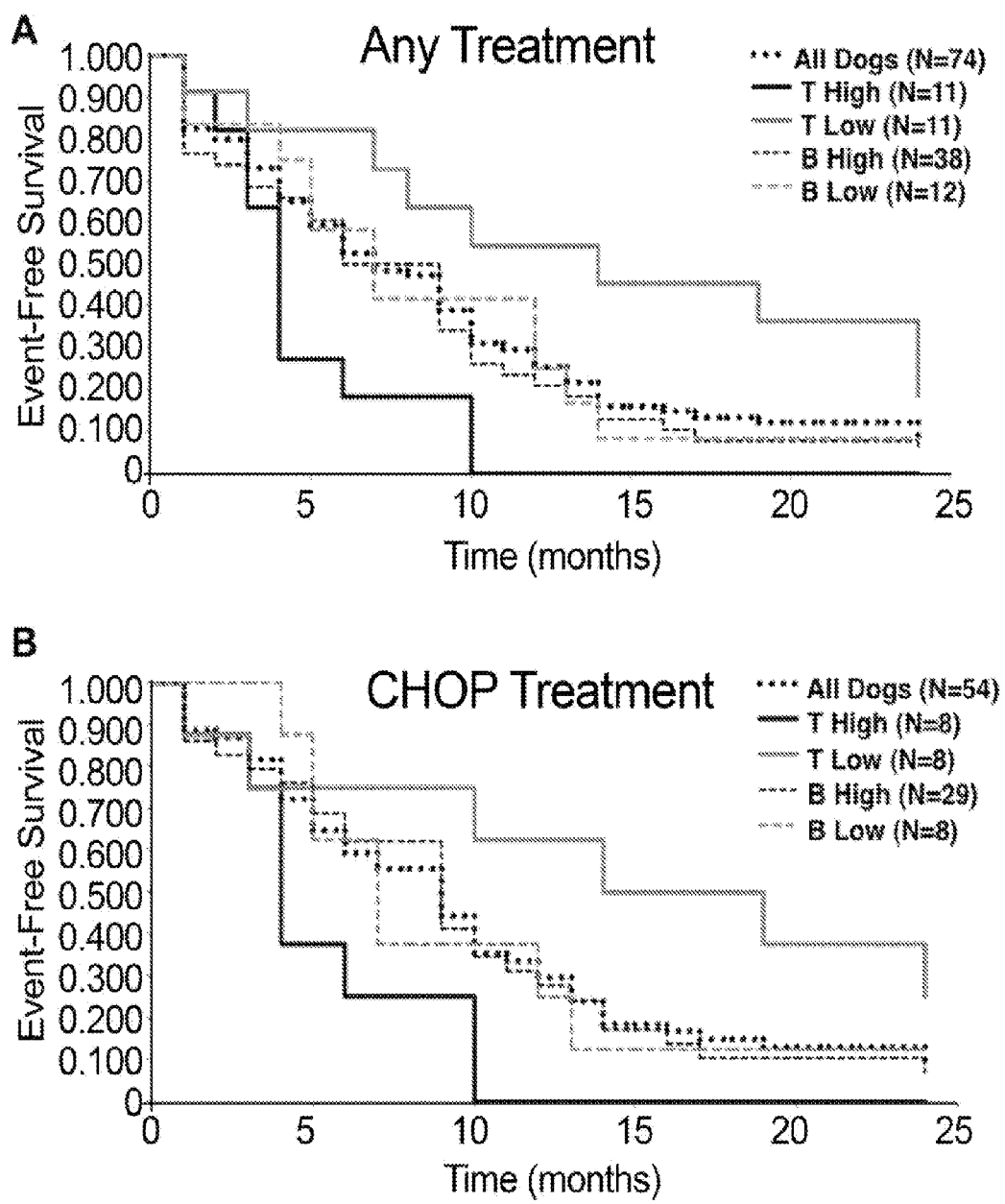
FIG. 5. Event-free survival is different for the three major molecular subtypes of canine lymphoma. Event-free survival data were available for 74 of 80 dogs recruited. (A) Kaplan-Meier event-free survival curves for dogs that received any treatment, classified according to molecular subgroups. (B) Kaplan-Meier event-free survival curves for dogs that received CHOP-based chemotherapy, classified according to molecular subgroups. The numbers in parenthesis to the right of each legend in both graphs represent sample size for the groups. Median survival for all treated dogs was 6.6 months, and for CHOP-treated dogs it was 8.5 months. Event-free survival of dogs with low-grade T-cell lymphoma was significantly longer (p<0.05) than that of dogs with high-grade T-cell lymphoma or dogs with B-cell lymphoma, regardless of treatment, as determined using the log-rank test. The event-free survival of dogs with high-grade T-cell lymphoma was significantly shorter (p<0.05)

Molecular Stratification Defines Subtypes of Disease that are Predictive for Event-Free Survival for Dogs with Lymphoma We showed previously that dogs with low-grade T-cell lymphoma had significantly longer overall survival times than either dogs with high-grade T-cell lymphoma or dogs with any B-cell lymphoma (Modiano et al. Leukemia. 2007; 21(1):184-187). Here, we re-examined the predictive value of this classification using event-free survival data (i.e., time from diagnosis to relapse), a more reliable indicator for outcome, from 80 dogs where 54 were treated with standard of care (multi-agent CHOP-based chemotherapy) and 20 were treated using single agent protocols, prednisone, or other palliative care measures. Treatment and outcome (relapse) data were not available for six dogs. The 74 evaluable dogs included 35 dogs used for the gene expression profiling experiment, as well as dogs collected as part of this contemporary effort, which allowed us to achieve statistical power to detect event-free survival differences among the different WHO groups. Kaplan-Meier survival probability curves for dogs that received any treatment or that received standard of care CHOP-based chemotherapy treated are shown in FIG. 5A and FIG. 5B, respectively. Survival times were longest for dogs with low-grade T-cell lymphomas (TZL), shortest for dogs with high-grade T-cell lymphomas (LBT and PTCL), and intermediate for dogs with B-cell lymphomas. The survival benefit for dogs with low-grade T-cell lymphomas treated with CHOP-based protocols (8 of 11 dogs) appeared to be modest. In contrast to what we observed with the T-cell subtypes, there was no significant difference in event-free (or overall) survival between high-grade B-cell malignancies and low-grade B-cell malignancies.

These data show concordance between the molecular profiles and the biological behavior of canine T-cell and B-cell lymphomas, and suggest that in the dog, the presence of non-malignant T-cells in MZLs may not be prognostically significant even though their presence has been correlated with favorable prognosis in human DLBCL (Alizadeh et al. Nature. 2000; 403(6769):503-511). In this cohort, BL cases were exquisitely responsive to CHOP-based chemotherapy (N=8; median survival=7 months; range=3-45 months), but the inclusion of these cases in the high-grade B-cell lymphoma group did not skew that group's survival significantly.

A Simplified Four-Biomarker Signature is Robust to Classify Molecular Subtypes of Lymphoma We next evaluated the potential to use a simplified profile of gene expression that could be translated into a diagnostic platform to rapidly and accurately distinguish among the three defined molecular groups. The array data showed that CD28 and ABCA5 consistently showed differential expression in T-cell lymphomas and B-cell lymphomas, and the ratio of gene expression for these two genes was sufficient to establish whether any particular tumor originated from the T-cell or from the B-cell lineage (FIG. 6A, Arrays 1 and 2). Similarly, the ratio of CCDC3 and SMOC2 expression was sufficient to classify T-cell tumors into "T-low" (TZL) or "T-high" (LBT or PTCL) categories (FIG. 6B, Arrays 1 and 2).

To validate this molecular approach of classification for canine lymphoma, we prospectively evaluated expression of these genes using qRT-PCR in an independent cohort of 17 cases to verify their utility to provide a definitive molecular classification. Samples were immunophenotyped and classified according to their morphologic appearance by a pathologist (TDO) without knowledge of the molecular results. For each sample, we first divided the value for CD28 expression over the value for ABCA5 expression. If the ratio was greater than 1, the tumor was determined to originate from a T cell; conversely, if the ratio was less than 1 the tumor was determined to originate from a B cell (FIG. 6A, qRT-PCR). For each T-cell tumor, we then divided the value for CCDC3 expression over the value for SMOC2 expression. If the ratio was greater than 1, the tumor was classified as a low-grade T-cell lymphoma, and if the ratio was less than 1 the tumor was classified as a high-grade T-cell lymphoma (FIG. 6B, qRT-PCR). Using this test, we correctly classified 17/17 samples into the correct phenotype (B or T cell), suggesting the probability of obtaining an incorrect classification using this algorithm is less than 1 in 1,000,000,000 (Fisher's Exact testp=$8 \times 10^{-10}$). We similarly classified 9/9 samples into the correct T-high or T-low subgroup, suggesting the probability of obtaining an incorrect classification using this algorithm is less than 1 in 10,000 (Fisher's Exact testp=$4 \times 10^{-5}$).

Thus, we provide a molecular classification scheme for subtypes of canine lymphoma. This is a significant step in our understanding of the disease and it complements morphological and topographical classification systems. It also allows comparisons between some types of canine lymphoma and human non-Hodgkin lymphoma (NHL), as it reveals a certain extent of disease homology between certain subtypes of canine lymphoma and human NHL.

DLBCL was one of the first human neoplasms for which molecular subtypes were defined (Alizadeh et al. Nature. 2000; 403(6769):503-511). This classification, which includes activated B-cell-like (ABC) DLBCL, germinal center B-cell-like (GCB) DLBCL, and primary mediastinal B-cell lymphoma (PMBL) has held up for over a decade with some refinement (Gutierrez-Garcia et al. Blood. 2011; 117(18):4836-4843; Staudt and Dave. Adv Immunol. 2005; 87:163-208), and it has been proposed that the three subtypes are distinct diseases originating from cells with mutations that affect different biochemical pathways (Lenz et al. Proc Natl Acad Sci USA. 2008; 105(36):13520-13525). Expression signatures for ABC DLBCL, GCB DLBCL, and PMBL DLBCL are correlated with survival, and they can be simplified for diagnostic purposes to tests utilizing six genes (Lossos et al. N Engl J Med. 2004; 350(18):1828-1837). Immunohistochemistry for a select group of proteins encoded as part of the DLBCL gene signature is thought to recapitulate the molecular classification and to robustly stratify GCB and non-GCB tumors, but recent data suggest that classification of human DLBCL based on immunohistochemistry is not predictive for response to treatment or for survival (Gutierrez-Garcia et al. Blood. 2011; 117(18):4836-4843; Rigacci et al. J Chemother. 2011; 23(4):227-231).

Less work has been done for other subtypes of human NHL, although at least one gene expression profiling data set is available in the public domain for virtually every common subtype of this disease (Gomez-Abad et al. Blood. 2011; 118(20):5517-5527; Iqbal et al. Blood. 2010; 115(5):1026-1036; Lenz et al. Proc Natl Acad Sci USA. 2008; 105(36): 13520-13525; Piccaluga et al. Blood. 2011; 117(13):3596-3608; Raetz et al. Pediatr Blood Cancer. 2006; 47(2):130-140).

Here, we identify molecular correlates for common morphological subtypes of canine lymphoma classified using the modified WHO classification. Our data show that the most common subtypes of canine lymphoma (DLBCL, MZL, LBT, PTCL, and TZL) (Valli et al. Vet Pathol. 2011; 48(1):198-211) can be generally subdivided into three molecular subgroups: high-grade T-cell lymphomas (LBT, PTCL), low-grade T-cell lymphomas (TZL), and B-cell lymphomas (DLBCL and MZL) Our data set included two samples of BL, which were generally indistinguishable from DLBCL using gene expression profiles, as well as one NTNBL sample, which was most similar to the TZL samples, but nevertheless appeared to be definable as its own entity using principal component analysis.

The classification of samples into three major groups was prognostically significant. TZLs have been reported to show indolent progression (Valli et al. Vet Pathol. 2006; 43(3): 241-256), and our results here and elsewhere (Modiano et al. Leukemia. 2007; 21(1):184-187) support that observation. These tumors might initially benefit from conservative management (e.g., watchful waiting) or low intensity chemotherapy that would reduce the likelihood of treatment-related toxicity with low risk for accelerated tumor progression. In contrast, high-grade LBTs and PTCLs can be aggressive, rapidly progressive tumors that respond poorly to conventional chemotherapy. This information undoubtedly can help dog owners and veterinarians make more educated treatment decisions, but its intrinsic benefit has yet to outweigh common resistance to biopsy procedures. Moreover, genome-wide gene expression profiling can be cost-prohibitive and/or impractical.

Thus, we developed a simple and reliable qRT-PCR based test to provide preliminary stratification of canine lymphomas into the classes of B-cell lymphomas, low-grade T-cell lymphomas, or high-grade T-cell lymphomas. This test can be performed using fine needle aspirate samples preserved at the point of care, potentially improving our diagnostic capability with acceptable risk and with favorable assessments of cost and benefit.

We identified a robust four-biomarker signature (CD28, ABCA5, CCDC3, SMOC2) that permits one to stratify canine lymphoma into three clinically-relevant groups. Other signatures using other biomarkers also may be successful for stratifying subgroups of malignancies. Thus, the four-biomarker signature described herein is merely exemplary. The method described herein may be performed analyzing any set of two or more biomarkers that adequately stratify clinically relevant subtypes of disease. Adequate stratification can reflect any clinically acceptable level of predictive accuracy. The accuracy of a biomarker signature may be evaluated using the formula:

$$\% \text{ accuracy} = \frac{\text{Correct results}}{(\text{Correct results} + \text{false positives} + \text{false negatives})}$$

A particular biomarker signature can be considered to adequately stratify clinically relevant subtypes of disease if the biomarker signature possesses at least 70% accuracy such as, for example, at least 75% accuracy, at least 80% accuracy, at least 81% accuracy, at least 82% accuracy, at least 83% accuracy, at least 84% accuracy, at least 85% accuracy, at least 86% accuracy, at least 87% accuracy, at least 88% accuracy, at least 89% accuracy, at least 90% accuracy, at least 91% accuracy, at least 92% accuracy, at least 93% accuracy, at least 94% accuracy, at least 95% accuracy, at least 96% accuracy, at least 97% accuracy, at least 98% accuracy, at least 99% accuracy, or 100% accuracy. In certain embodiments, for example, a biomarker signature using CD28 and ABCA5 stratifies T-cell tumors from B-cell tumors with 100% accuracy. (FIG. 6A). As another example, a biomarker signature using CCDC3 and SMOC2 stratifies high grade T-cell tumors from low grade T-cell tumors with 100% accuracy. (FIG. 6B).

One of the genes expressed at higher levels in TZL (T-low) compared to LBT and PTCL (T-high) was CR2 (complement receptor-2 or CD21). This result confirms bona fide subsets of T-cell malignancies in dogs—as opposed to, for example, an unusually high proportion of tumors with bi-lineage differentiation. This result also may explain, at least in part, the observed reactivity of a widely used anti-CD21 antibody, which is conventionally used as a B-cell marker, in canine lymphomas that also express CD3 and CD5.

In the case of B-cell lymphomas, we observed molecular similarity between DLBCL and MZL. Among all the canine lymphoma subtypes defined by the WHO classification, DLBCL and nodal MZL are the most challenging to distinguish (Valli. Cancer Therapy. 2008; 6:221-226), and our data suggest that these conditions may represent a continuum of the same disease. We have observed similar patterns using DNA copy number abnormalities to classify canine B-cell lymphomas (R. Thomas, et al, manuscript in preparation). The clustering of BL with these two groups, however, is somewhat surprising. BL has distinguishable morphological characteristics (Ponce et al. Vet Pathol. 2010; 47(3):414-433; Valli et al. *Classification of Hematopoietic Tumors of Domestic Animals*, Second Series ed. AFIP— American Registry of Pathology, Washington, D.C., 2002; Valli et al. Vet Pathol. 2011; 48(1):198-211; Wright et al. Proc Natl Acad Sci USA. 2003; 100(17):9991-9996), and it can also be defined by the peculiar translocation t(11; 13) involving the immunoglobulin heavy (IGH) locus in canine chromosome 11 (CFA 11) and the MYC locus in CFA 13 (Breen and Modiano. Chromosome Res. 2008; 16(1):145-154). Unlike what we observed in this study, Ponce et al reported survival for BL cases was measured in weeks (Ponce et al. Vet Pathol. 2010; 47(3):414-433). This suggests that there may be molecular heterogeneity in BL and that additional diagnostics to confirm the presence of a t(11; 13) translocation may be advisable to confirm this diagnosis and to predict treatment responses. Other cytogenetic tests may similarly be able to predict treatment responses in other subtypes of canine malignant lymphoma (M. Breen, unpublished results).

It is possible that the gene signature that defines DLBCL, MZL, and BL is a product of c-Myc overexpression. BLs have an activating MYC translocation, and DLBCLs and MZLs show recurrent copy number gains of CFA 13, including the MYC locus (Thomas et al. Leuk Lymphoma. 2011; 52(7):1321-1335). Preliminary analyses using the Ingenuity Pathway Analysis transcription factor module suggest that a major difference between T-cell lymphomas and B-cell lymphomas can involve differential Myc activity, based on the abundance of highly expressed Myc targets in B-cell tumors and their absence in T-cell tumors. It is also possible that the cells that give rise to canine DLBCL and MZL are functionally and topographically related, originating from the germinal or follicle center, and thus share immunophenotypic and molecular activation markers despite different degrees of anatomical lymph node effacement and slightly to moderately different morphologic appearance.

Comparative analyses of human and canine MZL and DLBCL showed similar groupings and conserved driver genes. Together, the data from the human and canine cohorts suggest that these two conditions represent a continuum of one disease in both species. The enrichment of cell cycle-related pathways in high grade B-cell lymphomas suggests that analysis of a larger sample set of tumors might provide a robust basis to refine segregation between DLBCL and MZL even if they represent distinct stages of the same disease. We showed previously that a related cell-cycle signature was useful to stratify canine and human osteosarcomas according to their biological behavior in vivo (Scott et al. Bone. 2011; 49(3):356-367), and preliminary data indicate that similar transcription factors may be dysregulated in both diseases.

We observed enrichment of gene sets associated with activated T cells in MZL samples. This result was consistent with the quantifiable excess of T cells seen in MZL samples by flow cytometry, and the frequent identification of T cell aggregates by immunohistochemistry. This could be explained by the presence of residual T cells in lymph nodes that have not undergone complete effacement (indolent disease) or by recruitment of infiltrating T cells. The latter could be effector (inflammatory) T cells responding to anatomical disruption or immunological cues, or they could be regulatory T cells co-opted by the tumor to mitigate inflammation and antitumor immune responses. The enriched T-cell associated gene sets we found were most consistent with regulatory T cells, which might provide independent explanations both for the presence of T cells in MZL samples and for the rather "poor" survival seen in some dogs diagnosed with this otherwise "indolent" disease.

In summary, we have shown that canine lymphoma can be stratified into at least three molecular subgroups that are prognostically significant, and we have developed a robust test to establish this classification measuring the standardized expression of four genes.

Thus, in one aspect, this disclosure describes a method a method that distinguishes between subtype of canine lymphoma. Generally, the method includes analyzing a tumor tissue sample from a subject for expression of at least two biomarkers. The ratio of expression between the biomarkers identifies the tumor tissue sample as coming from a subject having a particular subtype of lymphoma. The tumor tissue sample may be any suitable form of tissue sample that includes a plurality of lymphoma cells. Exemplary types of tissue samples include, for example, a biopsy sample or a fine needle aspirate sample.

The expression of the biomarkers may be measured using any suitable method for measuring gene expression. As used herein, "gene expression" involves transcription of at least a portion of genomic DNA (e.g., at least a portion of a coding region—i.e., at least portion of genomic DNA that encodes a polypeptide) to form RNA (i.e., a transcript, or mRNA), which may be translated by ribosomes into a polypeptide (e.g., a protein). Assessing gene expression can be done by determining cellular RNA levels or protein levels in a cell. Various methods for measuring gene expression at the RNA level or protein level are known. Exemplary methods for measuring RNA levels include, for example, Northern blotting, nuclease protection assays, DNA microarrays, serial analysis of gene expression, quantitative reverse transcription-polymerase chain reaction (qRT-PCR), differential-display RT-PCR, massively parallel signature sequencing, and the like. In particular, measuring gene expression at the RNA level can be performed using real-time quantitative RT-PCR assay such as, for example, exonuclease-based assays, for example, TaqMan® assays. Exemplary methods of measuring protein expression levels include, for example, mass spectrometry, two-dimensional gel electrophoresis, antibody microarrays, tissue microarrays, ELISA, radioimmunoassay, immuno-PCR, Western blotting, flow cytometry, FACS (fluorescence activated cell sorting), immunohistology, immunocytology, and the like. For immunoassays, antibodies that specifically bind, for example, CD28, ABCA5, CCDC3, or SMOC2 of multiple species, including canine species, are commercially available. In addition, a monoclonal antibody that specifically binds canine CD28 is described in, for example, Graves et al., Transplantation 2011, 91(8):833-840. In one particular embodiment, gene expression may be analyzed using qRT-PCR.

In some embodiments, the biomarkers whose expression is analyzed can include, for example, CD28 and ABCA5. The ratio of gene expression between CD28 and ABCA5 can distinguish between a B-cell lymphoma and a T-cell lymphoma. For example, a CD28:ABCA5 expression ratio greater than 1.0 indicates that the tumor tissue sample was obtained from a subject having a T-cell tumor such as, for example, lymphoblastic T-cell lymphoma, T-zone lymphoma, or peripheral T-cell lymphoma, not otherwise specified. Conversely, a CD28:ABCA5 expression ratio less than 1.0 indicates that the tumor tissue sample was obtained from a subject having a B-cell tumor such as, for example, Burkitt's lymphoma, diffuse large B-cell lymphoma, or marginal B-cell lymphoma.

In some embodiments, the biomarkers whose expression is analyzed can include, for example, CCDC3 and SMOC2. The ratio of gene expression between CCDC3 and SMOC2 can distinguish between high grade T-cell lymphomas and low-grade T-cell lymphomas. For example, a CCDC3:SMOC2 expression ratio of greater than 1.0 indicates that the sample was obtained from a subject having a low grade T-cell tumor such as, for example, T-zone lymphoma. Conversely, a CCDC3:SMOC2 expression ratio of less than 1.0 indicates that the sample was obtained from a subject having a high grade T-cell tumor such as, for example, lymphoblastic T-cell lymphoma or peripheral T-cell lymphoma, not otherwise specified.

One feature of the analysis described above is that the result is expressed as a simple ratio of gene expression from a single cell population. Thus, raw data need not be normalized to a reference value and one need not be concerned with the precise, absolute level of expression of any single gene in the analysis. Consequently, in many embodiments, the analysis may be performed without having to perform a control. Still, the analysis is capable of significant accuracy. FIG. 6 illustrates data demonstrating that the molecular analysis described herein agrees with a blinded analysis by a pathologist: the molecular analysis agreed with the blinded pathologist's analysis in 17 of 17 samples with respect to the correct phenotype (B cell versus T cell), and also in 9 of 9 samples with respect to T-high subgroup versus T-low subgroup.

In some embodiments, the method can further include providing therapy appropriate for the indicated lymphoma subgroup. For example, in some embodiments, one can provide conservative treatment to a subject identified as having a low grade T-cell tumor. As another example, one can provide aggressive treatment to a subject having a high grade T-cell tumor. As yet another example, one can provide standard of care treatment to a subject having a B-cell tumor. As used herein, "conservative treatment" refers to a regimen that can include, for example, no treatment, watchful waiting, administering prednisone to the subject, and administering chlorambucil to the subject. In some embodiments, one can administer to the subject a combination of chlorambucil and prednisone to the subject, a therapy regiment sometimes referred to as CP therapy. As used herein, "aggressive treatment" can include administering lomustine to the subject and administering adriamycin to the subject. As used herein, "standard of care" refers to a regiment that include, for example, CHOP or L-CHOP. CHOP refers to a treatment regimen that includes administering to the subject a combination of cyclophosphamide, adriamycin, vincristine, and prednisone. L-CHOP refers to the CHOP regimen, further including administering L-asparaginase to the subject. In some of these embodiments, L-CHOP may not necessarily improve the outcome of the therapy, but may decrease the time of therapy required to reach a desired outcome.

Thus, the gene expression analysis described herein can guide decision-makers toward a treatment regimen that provides an appropriate therapeutic outcome while minimizing undesirable side effects that may be associated with more aggressive treatment regimens. Moreover, at least one study concludes that for indolent tumors such as the low grade T-cell lymphomas, providing a treatment regimen more aggressive than conservative treatment does not necessarily improve the expected outcome (Flood-Knapik et al. Vet. Compar. Oncol. 2012; DOI: 10.1111/j.1476-5829.2011.00317.x). Thus, providing more aggressive therapy than is necessary may expose a subject to negative side effects without any potential therapeutic benefit.

In another aspect, this disclosure describes a kit for performing the method described immediately above. Generally, the kit can include reagents for measuring expression of a plurality of predictive coding regions in a sample from the subject. In some cases, the predictive genes can include, for example, a combination of CD28 and ABCA5—e.g., to distinguish between T-cell lymphomas and B-cell lymphomas. In other embodiments, the predictive genes can include, for example, a combination of CCDC3 and SMOC2 e.g., to distinguish between high-grade T-cell lymphomas and low-grade T-cell lymphomas. The kit can include reagents for performing Northern blotting, nuclease protection assay, DNA microarray, serial analysis of gene expression, quantitative reverse transcription-polymerase chain reaction (qRT-PCR), differential-display RT-PCR, massively parallel signature sequencing, or real-time quantitative PCR. In other embodiments, the kit can include reagents for performing protein expression analysis.

In the preceding description, particular embodiments may be described in isolation for clarity. Unless otherwise expressly specified that the features of a particular embodiment are incompatible with the features of another embodiment, certain embodiment can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials and Methods

Samples.

Samples from dogs with naturally occurring lymphoma (N=80) were collected from veterinary practices across the United States between 1999 and 2010 as described (Breen and Modiano. Chromosome Res. 2008; 16(1):145-154; Fosmire et al. Vet Pathol. 2007; 44(4):467-478; Ito et al. J Vet Intern Med. 2011; 25(4):890-896; Ito et al. Leuk Lymphoma. 2012; 53(7):1390-1398; Jubala et al. Vet Pathol. 2005; 42(4):468-476; Thomas et al. Leuk Lymphoma. 2011; 52(7):1321-1335). Animal care and experimentation were carried out in accordance with all applicable institutional, local, and national guidelines; dogs were under the care of licensed veterinarians and participation did not influence decisions of care. Sample collection protocols were approved and reviewed by the institutional review board of the University of Colorado and the institutional animal care and use committee of the University of Minnesota. Tumors from 35 dogs were processed as independent cohorts of 29 samples (cohort-1) and six additional samples (cohort 2) for gene expression profiling on microarrays. Samples from each cohort were handled and arrayed in separate batches by two individuals. Tumors were classified according to the modified WHO criteria based on morphology and immunophenotype (Valli et al. Vet Pathol. 2011; 48(1):198-211). The sample population was purposefully biased to Golden Retrievers, although it closely reflected the demographic distribution of lymphoma subtypes in the canine population as a whole (Valli et al. Vet Pathol. 2011; 48(1):198-211). Table 5 shows the demographic characteristics, treatment, and breed distribution for the dogs. Demographics of dogs profiled using microarray were not significantly different from dogs not included on array (p>0.4). For survival data, treatment protocols were summarized into three groups: 1) none, 2) palliative (prednisone only), or 3) multi-agent CHOP-based chemotherapy. For group 3, all CHOP-based protocols were considered equivalent based existing outcome data (Garrett et al. J Vet Intern Med. 2002; 16(6):704-709; Rassnick et al. J Vet Intern Med. 2007; 21(6):1364-1373; Soremno et al. Vet Comp Oncol. 2010; 8(3):196-208).

TABLE 5

Demographic characteristics of complete cohort of 80 dogs with lymphoma and restricted group of 35 dogs analyzed by gene expression profiling

|  | Recruited Cohort (N-80) Number (%) | GEP Cohort (N = 35)* Number (%) | Dogs not on Array (N = 45) Number (%) |
|---|---|---|---|
| SEX |  |  |  |
| Male | 48 (60) | 15 (43) | 33 (73) |
| Female | 32 (40) | 20 (57) | 12 (27) |
| AGE (years) |  |  |  |
| Median age at diagnosis | 8.5 | 8 | 8.8 |
| Mean age at diagnosis (± S.D.) | 8.5 (3.1) | 7.9 (3.3) | 8.1 (3.0) |
| Breed |  |  |  |
| Golden Retrievers | 50 (62) | 23 (66) | 27 (60) |
| All other breed[#] | 30 (38) | 12 (34) | 18 (40) |
| Classification |  |  |  |
| LBT | 9 | 5 | 4 |
| PTCL | 5 | 4 | 1 |
| TZL | 12 | 8 | 4 |
| T-ALCL | 1 | 0 | 1 |
| DLBCL | 29 | 10 | 19 |
| BL | 8 | 2 | 6 |
| MZL | 13 | 5 | 8 |
| B-ALCL | 2 | 0 | 2 |
| NTNBL | 1 | 1 | 0 |
| Median Survival (months) |  |  |  |
| All dogs | 6.6 (N = 80) | 8 (N = 35) | 6.2 (N = 45) |
| Standard of care | 8.5 (N = 54) | 10.0 (N = 22) | 8.0 (N = 32) |
| Other treatment | 6.1 (N = 15) | 10.5 (N = 5) | 5.6 (N = 8) |
| No treatment | 0.25 (N = 5) | 3.1 (N = 2) | 0.03 (N = 3) |

*GEP Cohort was divided into two groups with 29 and 6 dogs respectively. The demographic data for the two cohorts was not significantly different; the group of 6 dogs included 1 PTCL, 3 TZL, and 2 DLBCL
[#]Airedale Terrier (N = 1), Beagle (N = 2), Bichon Frise (N = 1), Boxer (N = 4), Labrador Retriever (N = 6), Mastiff (N = 3), Rottweiler (N = 4), Scottish Terrier (N = 1), Shih Tzu (N = 1), Terrier (N = 1), Toy Poodle (N = 1), West Highland Terrier (N = 1), Mix Breed (N = 2), Unknown (N = 2)
^LBT = lymphoblastic T-cell lymphoma, PTCL = peripheral T-cell lymphoma, not otherwise specified, TZL = T-zone lymphoma, ALCL = anaplastic large cell lymphoma, DLBCL = diffuse large B-cell lymphoma, BL = Burkitt's lymphomas, MZL = marginal-zone lymphoma, NTNBL = non-T, non-B-cell lymphoma RNA Isolation and Array Hybridization.

Biopsy samples were processed to single cell suspensions. Briefly, each biopsy sample was mechanically disrupted and passed through 80-μm mesh filters to eliminate stromal components. Cells were washed and a sufficient number was removed for immunologic characterization with the residual material cryopreserved in liquid nitrogen in 1-ml aliquots containing $1-5 \times 10^7$ cells in 90% fetal bovine serum (FBS) and 10% dimethyl sulfoxide (DMSO). RNA was isolated from cells recovered from cryopreservation using the RNAeasy Mini Kit and QIAshredder (QIAGEN, Valencia, Calif.). RNA concentration was determined using NanoDrop ND-1000 UV-Vis spectrophotometer (NanoDrop Technologies, Wilmington, Del.) and quality was measured using a 2100 Bioanalyzer (Agilent, Santa Clara, Calif.). All the samples included in the gene expression profiling experiment were suitable for microarray analysis based on RNA quality (RIN>7.0). Samples were hybridized to Affymetrix Canine 2.0 gene chips (Affymetrix, Santa Clara, Calif.) as described elsewhere (Tamburini et al. PLoS ONE. 2009; 4(5):e5549). A technical replicate of one sample was performed.

Array Data Analysis.

Following hybridization, each chip passed quality assurance and control procedures using the Affymetrix quality control algorithms provided in Expressionist Refiner module (Genedata AG, Basel, Switzerland). Probe signal levels were quantile-normalized and summarized using the GeneChip—Robust Multichip Averaging (GC-RMA) algorithm (Irizarry et al. Bioinformatics. 2006; 22(7):789-794). Normalized files were imported into Partek (Partek Inc., St. Louis, Mo., USA) and into the Expressionist Analyst module for principal component analysis (PCA), unsupervised clustering, and to assess significant differences in gene expression. The data generated by both programs showed consistent patterns. There are no precise tests to develop sample size estimates for gene expression profiling, so we started with theoretical principles and then applied empirical observations to support the sample size for these experiments a priori. The Canine 2.0 gene expression chip contains approximately 43,000 annotated sequences derived from the 7.56× canine genome (Lindblad-Toh et al. Nature. 2005; 438(7069):803-819). These represent virtually every known gene and a complement of expressed sequence tags that provide strong redundancy for expression profiling. We next considered that False Discovery Rate statistical analysis provided a suitable method to set thresholds for significance of elevated or reduced gene expression, but additional multivariate analyses and gene set enrichment would add further value to the analysis. We anticipated the data might not be normally distributed; so, non-parametric tests might be needed. As there is no analytical estimate of the power of the Kruskal-Wallis test after false discovery rate corrections, an approximation is useful in the case of small sample sizes. We can estimate the proportion of times when perfect rank separation between conditions might occur by chance as $2N!N!/(2N)!$, where N is the number of samples in each group. The Power Atlas (poweratlas.org; University of Alabama at Birmingham, Birmingham, Ala.), allowed us to obtain an empirical estimate that the imbalanced sample sets used for these experiments should provide greater than 90% power at $p=0.05$ to identify true positives, although the power to identify true negatives could be lower.

The correlation coefficient ($r^2$) for expression values of all probes between the duplicated samples was greater than 0.95. Probe IDs were mapped to corresponding canine Entrez Gene IDs using Affymetrix NetAffx EntrezGene Annotation. Prior to hierarchical clustering, normalized chip data were median-centered and $\log_2$-transformed. The possibility that breed was a significant driver for gene expression profiling was examined using supervised methods (Golden Retriever vs. non-Golden Retriever) and the False Discovery Rate. Supervised groups included all tumors from Golden Retrievers vs. non-Golden Retrievers, T-cell tumors from Golden Retrievers vs. non-Golden Retrievers, B-cell tumors from Golden Retrievers vs. non-Golden Retrievers, and DLBCLs from Golden Retrievers vs. non-Golden Retrievers. We similarly supervised data for other breeds with more than four samples in any of these comparisons. No genes showed statistically significant differential expression between these supervised groups even when the False Discovery Rate was 0.5 (one of every two genes predicted to be a false positive). Thus, we did not consider breed as a major component of subsequent analyses.

Unsupervised clustering was done using Gene Cluster 3.0 for Mac OS X (C Clustering Library 1.47, de Hoon et al., 2004, Bioinformatics 20(9):1453-1454) with correlation based on average linkage. Gene Cluster 3.0 data were visualized in Java TreeView (Saldanha. Bioinformatics. 2004; 20(17):3246-3248). Two group t-tests were done to determine genes that were differentially expressed between groups. Concerns about multiple hypothesis testing were addressed by requiring that differentially expressed genes show large fold changes (i.e., greater than 3-fold) and highly significant p-values <0.001. Though batch effects were discernible between the two cohorts, they did not affect analysis as each cohort was analyzed independently, with cohort-1 used as a training-set and cohort-2 used as a validation-set. Gene expression data were deposited in Gene Expression Omnibus (GEO).

Cross Species Bioinformatics.

We applied a method previously developed by our group to uncover conserved gene expression signatures in samples from different species (Scott et al. Bone. 2011; 49(3):356-367). We were unable to identify datasets from human T-cell NHL in GEO that were sufficiently robust to apply these algorithms. Thus, we only considered samples from B-cell NHL, and specifically from DLBCL and MZL for these analyses. We obtained all pertinent gene expression data and available patient metadata for DLBCL samples published by Lenz et al. (Proc Natl Acad Sci USA. 2008; 105(36):13520-13525) (GEO accession GSE11318). Data for each sample were normalized using GC-RMA and supervised into groups (ABC, GCB, PMBL, or unclassified) based on the patient metadata. Data for each subtype group were then mean centered and analyzed using PCA and hierarchical clustering. ABC and GCB groups were then analyzed using 2-group statistical testing for differentially expressed genes with a minimum fold change (effect size)≥3, and a Benjamin Hochberg (BH) q-value≤0.001. Similar procedures were used to extract gene lists from supplementary online materials or tabular data in two additional publications (Staudt and Dave. Adv Immunol. 2005; 87:163-208; Wright et al. Proc Natl Acad Sci USA. 2003; 100(17):9991-9996) and in United States Patent Application Publication No. 2011/0152115. With these resources we generated a list that included 95 differentially expressed genes between ABC and GCB subtypes of DLBCL. Of these 95 genes, 67 could be mapped to the canine genome using gene symbol information. This supervised list of 67 genes differentially expressed in human ABC and GCB DLBCL was then used to examine whether B-canine lymphomas conformed to this classification. We also used a set of DLBCL and MZL samples published by Gomez-Abad et al. (Blood. 2011; 118(20):5517-5527) (GEO accession GSE32018). The MZL and DLBCL samples were supervised into groups and analyzed using PCA and 2-group testing for differentially expressed genes with a p-value≤$10^{-6}$. Seventy-one differentially expressed genes were mapped to 56 canine genes by matching gene symbol name (15 were EST without sufficient annotation to map or lacked orthologous probes on the array of the opposing species). The 56 mapped canine genes were used for supervised clustering of samples within the canine dataset as described above. Conversely, 79 genes differentially expressed (p≤$10^{-3}$) between canine DLBCL and canine MZL were mapped to 70 human genes using the same gene symbol matching method as above and were subsequently used for supervised clustering of the human samples from the Gomez-Abad dataset.

Network Identification and Canonical Pathway Analysis of Differentially Expressed Genes.

Ingenuity Pathway Analysis (IPA) software (Ingenuity Systems, Redwood City, Calif.) was used to define functions and canonical pathways specifically enriched in the sets of genes using BH multiple testing corrections to assess significance (Scott et al. Bone. 2011; 49(3):356-367). Gene Set Enrichment Analysis (GSEA, Broad Institute, Cambridge, Mass.) was similarly used to define enriched functional pathways as described previously (Tamburini et al. PLoS ONE. 2009; 4(5):e5549). Statistical significance was estimated using phenotype-based permutations, with the attained p-values adjusted for multiple hypothesis testing.

Quantitative Real Time Reverse Transcriptase PCR (qRT-PCR).

Purified RNA was reverse transcribed to cDNA using the 1st Strand cDNA Synthesis Kit for RT-PCR (Roche Applied Science, Indianapolis, Ind.). qRT-PCR was used to quantify the resulting cDNAs in an ABI7500 sequence detector with the Taqman PCR Master Mix Protocol (ABI, Foster City, Calif.). Each reaction was performed by denaturing cDNAs at 95° C. for 10 minutes, followed by 40 PCR cycles of denaturation (95° C.) for 15 seconds, annealing (57° C.) for 30 seconds, and extension (68° C.) for 30 seconds per cycle. Primers were designed using Primer3 software (Rozen and Skaletsky. "HJ: Primer3 on the WWW for general users and for biologist programmers," in *Bioinformatics Methods and Protocols: Methods in Molecular Biology*, eds. Krawetz S, Misener S, pp. 365-386. Humana Press, Totowa, N.J., 2000). The primers used were: GAPDH F: GCCAAGAGGGTCAT-CATCTC (SEQ ID NO:1), R: CTTTGGCTAGAGGTGC-CAAG (SEQ ID NO:2); CD28, F: GACCACCGTTAGCA-CAATGA (SEQ ID NO:3), R: CCGGAACTCCTTTGAGAAGA (SEQ ID NO:4); ABCA5 F: TGGCCATTCATATCGTAGCA (SEQ ID NO:5), R: CGCAGCTACTTTGAGGGAAT (SEQ ID NO:6); SMOC2 F: GCTGGAGACCCAACCTCA (SEQ ID NO:7), R: ATTGGTTTTGTTCTGCCGACT (SEQ ID NO:8); CCDC3 F: TGTTTTCCAGCCTTTTCCAG (SEQ ID NO:9), R: GCTGCTTGTTACGCTTCTCC (SEQ ID NO:10). Validation of microarray data was performed by plotting log-transformed array values against log-transformed values of fold change in expression from five dogs using qRT-PCR for IKBKE F: CATCAAGCCTGGAAACATCA (SEQ ID NO:11), R: TTACCCCGAATGTCTTCTGC (SEQ ID NO:12) and IL17Ra F: TCCTTCATCCCCAAAAGATG (SEQ ID NO:13), R: TTGGTGTTCAGTTGCAGGAC (SEQ ID NO:14). The relationship between array and qRT-PCR values for the transcripts of interest was analyzed using Pearson's correlation (Scott et al. Bone. 2011; 49(3):356-367).

Immunophenotyping.

Flow cytometry, immunohistochemistry (IHC), and PCR for antigen receptor rearrangement (PARR) were used to phenotype tumors and to identify subpopulations in the tumors. Flow cytometry (Ito et al. J Vet Intern Med. 2011; 25(4):890-896; Jubala et al. Vet Pathol. 2005; 42(4):468-476), IHC (Jubala et al. Vet Pathol. 2005; 42(4):468-476) and PARR methods (Ito et al. J Vet Intern Med. 2011; 25(4):890-896) have been described previously. Immunohistochemistry was done by IHC Services (Smithville, Tex.), and confirmatory staining was done as needed at the Masonic Cancer Center Shared Pathology Resource core facility. PARR was done by the Immunopathology Laboratory of Colorado State University (Ft. Collins, Colo.) and confirmatory analyses were done in the authors' laboratory at the University of Minnesota as needed.

Statistics.

Descriptive statistics for variables of breed, gender, age at diagnosis, and treatment regimen were performed. Categorical data are expressed as percentages, while continuous data are expressed as means±S.D., medians, and/or ranges. Fisher's exact test was performed to compare data from lymphoma subtypes and from the dogs used for gene expression profiling and the rest of the dogs in the recruitment cohort. Event-free survival (EFS) was defined as the interval from diagnosis until recurrence (relapse). In most cases, dogs were euthanized at the time recurrence was diagnosed. Censoring was done for dogs that received rescue therapy (on the date that recurrence was detected), for dogs that were lost to follow-up (on the last contact date), and for dogs that died from other causes (on the date of death). Kaplan-Meier analysis was done using a tool from the Walter and Elisa Hall Institute Department of Bioinformatics. Statistical significance was calculated using the log rank test and a p<0.05 was considered significant.

Diagnostic Algorithm.

Pairs of genes with potential diagnostic utility were chosen based on the following three criteria: 1) highly significant p-values between groups, 2) large and opposite fold-changes between groups, and 3) low intra-group variance within each of the groups that were to be separated. mRNA for 17 independent samples (not on the arrays) was quantified using qRT-PCR. The diagnostic algorithm consisted of applying the ration of gene-1/gene-2 to define a separation between B-cell tumors and T-cell tumors, and for the T-cell tumors a second level of separation between high-grade and low-grade lymphomas.

EXEMPLARY EMBODIMENTS

Embodiment 1

A method comprising: analyzing a tumor tissue sample from a subject for expression of at least two biomarkers, wherein a predetermined ratio of expression of the at least two biomarkers identifies the tumor tissue sample as coming from a subject having a particular subtype of lymphoma; and identifying the subject as having a particular subtype of lymphoma.

Embodiment 2

The method of Embodiment 1 wherein analyzing a tumor tissue sample from a subject for expression of at least two biomarkers comprises analyzing RNA.

Embodiment 3

The method of Embodiment 2 wherein analyzing RNA comprises qRT-PCR.

Embodiment 4

The method of Embodiment 1 wherein analyzing a tumor tissue sample from a subject for expression of at least two biomarkers comprises analyzing protein expression.

Embodiment 5

The method of any preceding Embodiment wherein the tissue sample comprises a fine needle aspirate sample or a biopsy sample.

Embodiment 6

The method of any preceding Embodiment wherein the at least two biomarkers comprise CD28 and ABCA5.

Embodiment 7

The method of Embodiment 6 wherein the predetermined ratio of expression between CD28 and ABCA5 is 1.0.

Embodiment 8

The method of Embodiment 7 wherein a CD28:ABCA5 expression ratio greater than 1.0 in the tumor tissue sample is indicative of a T-cell tumor.

Embodiment 9

The method of Embodiment 8 wherein the T-cell tumor comprises lymphoblastic T-cell lymphoma, T-zone lymphoma, or peripheral T-cell lymphoma, not otherwise specified.

Embodiment 10

The method of Embodiment 7 wherein a CD28:ABCA5 expression ratio less than 1.0 in the tumor tissue sample is indicative of a B-cell tumor.

Embodiment 11

The method of Embodiment 10 wherein the B-cell tumor comprises Burkitt's lymphoma, diffuse large B-cell lymphoma, or marginal B-cell lymphoma.

Embodiment 12

The method of any preceding Embodiment wherein the at least two biomarkers comprise CCDC3 and SMOC2.

Embodiment 13

The method of Embodiment 12 wherein the predetermined ratio of expression between CCDC3 and SMOC2 is 1.0.

Embodiment 14

The method of Embodiment 13 wherein a CCDC3:SMOC2 expression ratio of greater than 1.0 is indicative of a low grade T-cell tumor.

Embodiment 15

The method of Embodiment 14 wherein the low grade T-cell tumor comprises T-zone lymphoma.

Embodiment 16

The method of Embodiment 13 wherein a CCDC3:SMOC2 expression ratio of less than 1.0 is indicative of a high grade T-cell tumor.

Embodiment 17

The method of Embodiment 16 wherein the high grade T-cell tumor comprises lymphoblastic T-cell lymphoma or peripheral T-cell lymphoma, not otherwise specified.

Embodiment 18

The method of any preceding Embodiment wherein the at least two biomarkers are selected to identify the tumor tissue sample as coming from a subject having a particular subtype of lymphoma with at least 80% accuracy.

Embodiment 19

The method of any preceding Embodiment further comprising providing conservative treatment to a subject identified as having a low grade T-cell tumor, providing aggressive treatment to a subject having a high grade T-cell tumor, or standard of care treatment to a subject having a B-cell tumor.

Embodiment 20

The method of Embodiment 19 wherein conservative treatment comprises at least one of: watchful waiting, administering prednisone to the subject, and administering chlorambucil to the subject.

Embodiment 21

The method of Embodiment 120 wherein conservative treatment comprises administering to the subject a combination of prednisone and chlorambucil.

Embodiment 22

The method of Embodiment 19 wherein aggressive treatment comprises at least one of: administering lomustine to the subject and administering adriamycin to the subject.

Embodiment 23

The method of Embodiment 22 wherein aggressive treatment comprises administering to the subject a combination of lomustine and adriamycin.

Embodiment 24

The method of Embodiment 19 wherein standard of care comprises administering to the subject a combination of cyclophosphamide, adriamycin, vincristine, and prednisone.

Embodiment 25

The method of Embodiment 24 further comprising administering to the subject L-asparaginase.

Embodiment 26

A kit for determining prognosis of a subject, the kit comprising: reagents for measuring expression of a plurality of predictive coding regions in a sample from the subject, the plurality of predictive coding regions comprising at least one of:
  a combination of CD28 and ABCA5; or
  a combination of CCDC3 and SMOC2.

Embodiment 27

The kit of Embodiment 26 wherein the reagents for measuring expression of a plurality of predictive coding regions comprises reagents for performing Northern blotting, nuclease protection assay, DNA microarray, serial analysis of gene expression, quantitative reverse transcription-polymerase chain reaction (RT-PCR), differential-display RT-PCR, massively parallel signature sequencing, or real-time quantitative PCR.

Embodiment 28

The kit of Embodiment 26 wherein the reagents for measuring expression of a plurality of predictive coding regions comprises reagents for performing protein expression analysis.

Embodiment 29

The use of a CD28 gene product in the manufacture of a composition for detecting B-cell lymphoma versus T-cell lymphoma in a tissue sample obtained from a subject.

Embodiment 30

The use of an ABCA5 gene product in the manufacture of a composition for detecting B-cell lymphoma versus T-cell lymphoma in a tissue sample obtained from a subject.

Embodiment 31

The use of a CCDC3 gene product in the manufacture of a composition for detecting high grade T-cell lymphoma versus low grade T-cell lymphoma in a tissue sample obtained from a subject.

Embodiment 32

The use of a SMOC2 gene product in the manufacture of a composition for detecting high grade T-cell lymphoma versus low grade T-cell lymphoma in a tissue sample obtained from a subject.

Embodiment 33

The use of any one of Embodiments 29-32 wherein the gene product comprises an RNA.

Embodiment 34

The use of any one of Embodiments 29-32 wherein the gene product comprises a protein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method to distinguish lymphomas comprising:
analyzing a tumor tissue sample from a subject for expression of CD28, ABCA5, CCDC3, and SMOC2,
calculating an expression ratio between CD28 and ABCA5;
calculating an expression ratio between CCDS3 and SMOC2;
wherein:
a CD28:ABCA5 expression ratio greater than 1.0 in the tumor sample is indicative of a T-cell tumor;
a CD28:ABCA5 expression ratio less than 1.0 in the tumor tissue sample is indicative of a B-cell tumor;
and if a T-cell tumor is indicated, wherein:
a CCDC3:SMOC2 expression ratio of greater than 1.0 is indicative of a low grade T-cell tumor; and
a CCDC3:SMOC2 expression ratio of less than 1.0 is indicative of a high grade T-cell tumor.

2. The method of claim 1 wherein analyzing a tumor tissue sample from a subject for expression of at least two biomarkers comprises analyzing RNA.

3. The method of claim 2 wherein analyzing RNA comprises qRT-PCR.

4. The method of claim 1 wherein analyzing a tumor tissue sample from a subject for expression of at least two biomarkers comprises analyzing protein expression.

5. The method of claim 1 wherein the tissue sample comprises a fine needle aspirate sample or a biopsy sample.

6. The method of claim 1 wherein the T-cell tumor comprises lymphoblastic T-cell lymphoma, T-zone lymphoma, or peripheral T-cell lymphoma, not otherwise specified.

7. The method of claim 1 wherein the B-cell tumor comprises Burkitt's lymphoma, diffuse large B-cell lymphoma, or marginal B-cell lymphoma.

8. The method of claim 1 wherein the low grade T-cell tumor comprises T-zone lymphoma.

9. The method of claim 1 wherein the high grade T-cell tumor comprises lymphoblastic T-cell lymphoma or peripheral T-cell lymphoma, not otherwise specified.

10. The method of claim 1 further comprising providing conservative treatment to a subject identified as having a low grade T-cell tumor, providing aggressive treatment to a subject having a high grade T-cell tumor, or standard of care treatment to a subject having a B-cell tumor.

11. The method of claim 10 wherein conservative treatment comprises at least one of: watchful waiting, administering prednisone to the subject, and administering chlorambucil to the subject.

12. The method of claim 11 wherein conservative treatment comprises administering to the subject a combination of prednisone and chlorambucil.

13. The method of claim 10 wherein aggressive treatment comprises at least one of: administering lomustine to the subject and administering adriamycin to the subject.

14. The method of claim 13 wherein aggressive treatment comprises administering to the subject a combination of lomustine and adriamycin.

* * * * *